(12) United States Patent
Chopra et al.

(10) Patent No.: US 6,365,560 B1
(45) Date of Patent: Apr. 2, 2002

(54) COMPOSITION COMPRISING TRICLOCARBAN OR TRICLOSAN

(75) Inventors: Suman K. Chopra, Dayton; Janine A. Chupa, Somerset; Amrit Patel, Dayton; Elizabeth K. Parle-Schmitz, Branchburg; Clarence Robbins, Martinsville, all of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/707,025

(22) Filed: Nov. 6, 2000

Related U.S. Application Data

(63) Continuation of application No. 09/388,641, filed on Sep. 2, 1999, now Pat. No. 6,156,713, which is a continuation of application No. 08/736,116, filed on Oct. 24, 1996, now Pat. No. 6,008,173.
(60) Provisional application No. 60/006,801, filed on Nov. 3, 1995.

(51) Int. Cl.⁷ ................................. A61K 7/50
(52) U.S. Cl. ...................... 510/141; 510/152; 510/155; 510/446; 510/447
(58) Field of Search ................. 510/130, 141, 510/151, 152, 155, 159; 424/70.21, 70.24, 75.19

(56) References Cited

U.S. PATENT DOCUMENTS

| | | |
|---|---|---|
| 3,761,418 A | 9/1973 | Parran |
| 4,686,060 A | 8/1987 | Crabtree et al. |
| 4,740,367 A | 4/1988 | Fores et al. |
| 4,954,335 A | 9/1990 | Janchipraponvej |
| 5,013,763 A | 5/1991 | Tubesing et al. |
| 5,059,414 A | 10/1991 | Dallal et al. |
| 5,064,555 A | 11/1991 | Medcalf et al. |
| 5,154,849 A * | 10/1992 | Visscher et al. ....... 252/174.15 |
| 5,308,526 A | 5/1994 | Dias et al. |
| 5,312,559 A | 5/1994 | Kacher et al. |
| 5,589,177 A * | 12/1996 | Herb et al. ................. 424/401 |

FOREIGN PATENT DOCUMENTS

| | | |
|---|---|---|
| EP | 58853 | 9/1982 |
| EP | 76146 | 4/1983 |
| EP | 194097 | 9/1986 |
| EP | 226337 | 6/1987 |
| EP | 308189 | 3/1988 |
| EP | 268982 | 6/1988 |
| EP | 366070 | 5/1990 |
| EP | 392320 | 10/1990 |
| EP | 432951 | 6/1991 |
| EP | 468721 | 1/1992 |
| EP | 529847 | 3/1993 |
| EP | 529883 | 3/1993 |
| EP | 530974 | 3/1993 |
| EP | 578481 | 1/1994 |
| WO | 9210162 | 6/1992 |
| WO | 9309761 | 5/1993 |
| WO | 9403150 | 2/1994 |
| WO | 9403151 | 2/1994 |
| WO | 9403152 | 2/1994 |
| WO | WO 9502388 | 1/1995 |
| WO | WO 9522311 | 8/1995 |
| WO | WO 9526710 | 10/1995 |

* cited by examiner

*Primary Examiner*—Necholus Ogden
(74) *Attorney, Agent, or Firm*—Martin B. Barancik

(57) ABSTRACT

A personal cleansing composition which comprises
 a. a skin cleansing effective amount of a surfactant or mixture of surfactants,
 b. a hydrophobic active component in quantities which brings about a perceived effect on the skin, said effect selected from the group consisting of skin conditioning, skin protection from irritants and antibacterial agents,
 c. a hydrocarbon containing component, and
 d. a cationic polymer
the quantities of c and d selected so that the effect on the skin by component b is enhanced over the additive effects of c and d alone.

12 Claims, No Drawings

COMPOSITION COMPRISING TRICLOCARBAN OR TRICLOSAN

This is a continuation of prior application Ser. No. 09/388,641 filed Sep. 2, 1999 now U.S. Pat. No. 6,156,713 which is a continuation of application Ser. No. 08/736,116 filed Oct. 24, 1996 now U.S. Pat. No. 6,008,175 which claims priority from U.S. provisional Serial No. 60/006,801 filed Nov. 3, 1995 which applications are incorporated herein by reference.

BACKGROUND OF THE INVENTION

Basic skin cleansing activities have been long addressed by the personal care industry. Removing soil from the skin is a worldwide requirement of the consumer population that has been met by the available skin cleansing products. The consumer population is now looking for additional benefits beyond basic cleansing. Skin conditioning i.e. smoothness, texture, etc., is a desired characteristic and brought about through the presence of emollients in a basic skin cleansing composition. Additionally, the presence of components which bring about an antibacterial effect on the skin are now becoming ever more acceptable and desirable by the consumer population.

In order for these effects to be perceived by the consumer or measurable to various degrees, there must be contact of the active ingredient which brings about the effect with the skin. Therefore, increased deposition of an active ingredient on the skin is certainly desirable since a greater effect should normally follow and less active ingredient may be employed, thereby potentially reducing the cost of the formulation.

A new way of increasing the deposition of hydrophobic active ingredients from skin cleansing compositions has been discovered. This provides both liquid and solid skin cleansing compositions with the ability to deliver greater quantities of active ingredients to the skin during an ordinary skin cleansing procedure and/or maintain them on the skin for a longer period of time.

SUMMARY OF THE INVENTION

In accordance with the invention, there is a personal cleansing composition which comprises
  a. a skin cleansing effective amount of a surfactant or mixture of surfactants,
  b. a hydrophobic active component in quantities which brings about a perceived effect on the skin, said effect selected from the group consisting of skin conditioning, skin protection from irritants and antibacterial agents,
  c. a hydrocarbon containing component, and
  d. a cationic polymer the quantities of c and d selected so that the effect on the skin by component b is enhanced over the additive effects of c and d alone.

Still further, there is a method for using the above identified composition for skin cleansing.

A further composition is a personal cleansing composition which comprises
  a. about 9 to about 90 wt. % of a surfactant or mixture of surfactants,
  b. about 0.01 to about 10 wt. % of a hydrophobic active component in quantities which brings about a perceived effect on the skin, said effect selected from the group consisting of skin conditioning, skin protection from irritants and antibacterial agents,
  c. about 0.5 to about 5 wt. % of a hydrocarbon containing component, and
  d. about 0.01 to about 3 wt. % of a cationic polymer.

DETAILED DESCRIPTION OF THE INVENTION

The compositions of this invention bring about an increased perceived effect on the skin from known positive skin affecting materials. Although not to be bound by this theory, it is believed that this perceived effect is brought about through the increased deposition of the skin affecting material on the skin surface, or in such juxtaposition to the skin surface that the material has an opportunity to provide its effect. Thus, more of the material is available to perform its specific action. Additionally, the material may be held on the surface of the skin or in juxtaposition to the skin for a longer period of time, thereby providing an effect for a greater duration of time. Both of these effects may be present or only one. It is clear therefore, that there are at least two parameters which are involved in the increased perceived effect of the material on the skin. The first effect is the activity of the material, for example, the degree of skin conditioning, the reduced irritation of the skin and the reduced quantity of measurable bacteria present on the skin. The second effect is the duration of such activity as measured by time. This latter effect is particularly important for a product whose composition is designed to be removed from the skin such as a facial and hand wash, a shower gel, and the like.

In line with the cleansing activity of the composition, there must be a skin cleansing effective amount of a surfactant present in the composition. Soap, a long chain alkyl or alkenyl, branched or normal carboxylic acid salt such as sodium, potassium, ammonium or substituted ammonium salt, can be present in the composition. Exemplary of long chain alkyl or alkenyl are from about 8 to about 22 carbon atoms in length, specifically about 10 to about 20 carbon atoms in length, more specifically alkyl and most specifically normal, or normal with little branching. Small quantities of olefinic bond(s) may be present in the predominantly alkyl sections, particularly if the source of the "alkyl" group is obtained from a natural product such as tallow, coconut oil and the like.

Other surfactants can be present in the composition as well. Examples of such surfactants are the anionic, amphoteric, nonionic and cationic surfactants. Examples of anionic zwitterionic surfactants include but are not limited to alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and the like.

Alkyl chains for these surfactants are $C_8$–$C_{22}$, preferably $C_{10}$–$C_{18}$, more preferably $C_{12}$–$C_{14}$.

Anionic nonsoap surfactants can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

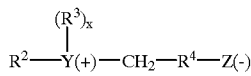

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; R3 is an alkyl or monohydroxyalkyl group containing 1 to about 3 carbon atoms; X is 1 when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; 5-[S-3-hydroxypropyl-S-hexadecylsulfonio] -3 hydroxypentane-1-sulfate; 3-[P,P-P-diethyl-P 3,6,9 trioxatetradecyl-phosphonio]-2-hydroxypropane-1-phosphate; 3-[N,N-dipropyl-N-3 dodecoxy-2-hydroxypropylammonio]-propane-1-phosphonate; 3-(N,N-di-methyl-N-hexadecylammonio) propane-1-sulfonate; 3-(N,N-dimethyl-N-hexadecylammonio)-2-hydroxypropane-1-sulfonate; 4-(N,N-di(2-hydroxyethyl)-N-(2 hydroxydodecyl) ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438, 091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, 1 auryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl) carboxymethyl betaine, oleyl dimethyl gamma-carboxypropyl betaine, lauryl bis-(2-hydro-xypropyl) alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:
stearyldimethylbenzyl ammonium chloride;
dodecyltrimethylammonium chloride;
nonylbenzylethyldimethyl ammonium nitrate;
tetradecylpyridinium bromide;
laurylpyridinium chloride;
cetylpyridinium chloride
laurylpyridinium chloride;
laurylisoquinolium bromide;
ditallow(Hydrogenated)dimethyl ammonium chloride;
dilauryldimethyl ammonium chloride; and
stearalkonium chloride.

Additional cationic surfactants are disclosed in U.S. Pat. No. 4,303,543 see column 4, lines 58 and column 5, lines 1–42, incorporated herein by references. Also see CTFA Cosmetic Ingredient Dictionary, 4th Edition 1991, pages 509–514 for various long chain alkyl cationic surfactants; incorporated herein by references.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl) amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyidimethylamine oxide, 3-dodecoxy-2-hydroxypropyldi(3-hydroxypropyl) amine oxide, dimethylhexadecylamine oxide.

5. Long chain tertiary phosphine oxides corresponding to the following general formula:

wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R'and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

Any quantity of surfactant or mixture of surfactant which brings about a skin cleansing effect can be employed in the composition of this invention. Generally, at least about 1 wt. % of the composition should be surfactant (a). Preferred minimums of at least about 3, 5, 7, 10, 20 and 30 wt. % surfactant(s) can be present in the composition. Maximum quantities of surfactant(s) depends upon the physical mixture of the composition being employed as well as the amount of components b, c and d therein. Generally, no more than about 95–97 wt. % surfactant(s) are present, specifically no more than about 90 wt. % surfactant(s). Maximum quantities of about 20, 30, 40, 50, 60, 70, 80, or 85 wt. % surfactant(s) can also be readily employed.

Component b is the hydrophobic material which provides the perceived effect to the skin. As used in this specification "hydrophobic" means a material which is more lipid soluble, that is non aqueous soluble, than aqueous soluble. It is preferred that the materials have little solubility in water and are essentially nonionic in character as opposed to ionic. Examples of such materials include but are not limited to emollients, antimicrobial agents, sunscreens, fragrances, insect repellents, anti fungal agents, and anti inflammatory agents.

Illustrative examples of emollients which are included within this invention are the long chain saturated or unsaturated fatty acids such as lauric, oleic, myristic, palmitic, stearic, branched as well as normal, silicones such as dimethyl silicones, methyl phenyl silicones, methyl higher alkyl silicones with the second alkyl group up to about 25 carbon atoms propoxylated silicones, all the silicones having a minimum viscosity of about 15,0000 centistoke, preferably about 40,000 centistoke and a maximum viscosity wherein the silicone remains fluid and is not yet a gum, lanolins, esters such as branched esters, for example, ethylhexyl palmitate, isopropyl stearate, isopropylmyristate, hexadecyl isodecyl or isopropyl ester of adipic, lactic, oleic, stearic, isostearic, myristic or linoleic acids; saturated and unsaturated fatty alcohols such as squalane and squalane, behenyl alcohol, hexadecanol; long chain esters such as stearylstearate, decylpalmitate, dodecyleicosanate and the like. Silicone gums are specifically excluded from this composition.

Examples of antibacterial agents which can be employed are the dicarbanilides, for example, triclocarban also known as trichlorocarbanilide CAS No. 101-20-2, triclosan, a halogenated diphenylether having CAS No. 3380-34-5, generally available as DP-300 from Ciba-Geigy; hexachlorophene, 3,4,5-tribromosalicylanilide, and salts of 2-pyridinethiol-1-oxide.

Organic sunscreens which act to ameliorate the effects of ultraviolet radiation on the skin can also be present in the composition. Illustrative examples of such materials include but are not limited to benzophenone, p-aminobenzoic acid, and octyldimethylparaamino benzoate.

The delivery system which brings about the enhanced deposition of the active hydrophobic skin affecting component b of the composition is a combination of the hydrocarbon containing component, c, and a cationic polymer, d.

Component c can be a typical hydrocarbonaceous material such as a wax, petrolatum, mineral oil, beeswax, a "permethyl" made up of longer chain branched hydrocarbons available from Permethyl Corporation. Permethyls are of the general formula

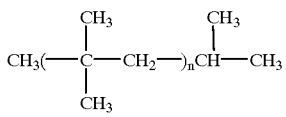

where n can vary from about 4 to over 200. Products where n=4, 16, 38, 214, respectively, are marketed as Permethyl 102A,104A, 106A and 1082A.

The petrolatum useful in the present invention can be any grade of white or yellow petrolatum recognized in the art as suitable for human application. Preferred petrolatum are those with a melting point in a range of from about 35° C. to about 500° C. The petrolatum of the composition can include hydrocarbon mixtures formulated with mineral oil and/or in combination with paraffin waxes of various melting points; all in small quantities compared to the petrolatum. A petrolatum without additional materials is preferred. Examples of waxes, particularly useful in solid compositions are microcrystalline waxes, generally those waxes which are known as paraffin wax, beeswax, and natural waxes derived from vegetables.

Cationic polymers is that generic class of materials which generally provide a positive skin feel to the skin during cleansing application, rinse off, and thereafter.

Cationic polymers includes but are not limited to the following groups:

(1) cationic polysaccharides;

(11) cationic copolymers of saccharides and synthetic cationic monomers, and (111) synthetic polymers selected from the group consisting of:

(A) cationic polyalkylene imines (B) cationic ethoxy polyalkylene imines (C) cationic poly[N-[3-(dimethylammonio)propyl]-N' [3-(ethyleneoxyethylene dimethylammonio)propyl] urea dichloride]

(D) in general a polymer having a quaternary ammonium or substituted ammonium ion.

The cationic polysaccharide class encompasses those polymers based on 5 or 6 carbon sugars and derivatives which have been made cationic by engrafting of cationic moieties onto the polysaccharide backbone. They may be composed of one type of sugar or of more than one type, i.e. copolymers of the above derivatives and cationic materials. The monomers may be in straight chain or branched chain geometric arrangements. Cationic polysaccharide polymers include the following: cationic celluloses and hydroxyethylcelluloses; cationic starches and hydroxyalkyl starches; cationic polymers based on arabinose monomers such as those which could be derived from arabinose vegetable gums; cationic polymers derived from xylose polymers found in materials such as wood, straw, cottonseed hulls, and corn cobs; cationic polymers derived from fucose polymers found as a component of cell walls in seaweed; cationic polymers derived from fructose polymers such as Inulin found in certain plants; cationic polymers based on acid-containing sugars such as galacturonic acid and glucuronic acid; cationic polymers based on amine sugars such as galactosamine and glucosamine; cationic polymers based on 5 and 6 membered ring polyalcohols; cationic polymers based on galactose monomers which occur in plant gums and mucilages; cationic polymers based on mannose monomers such as those found in plants, yeasts, and red algae; cationic polymers based on galactommannan copolymer known as guar gum obtained from the endosperm of the guar bean.

Specific examples of members of the cationic polysaccharide class include the cationic hydroxyethyl cellulose JR 400 made by Union Carbide Corporation; the cationic starches Stalok® 100, 200, 300, and 400 made by Staley, Inc.; the cationic galactomannans based on guar gum of the Galactasol 800 series by Henkel, Inc. and the Jaguar Series by Celanese Corporation.

The cationic copolymers of saccharides and synthetic cationic monomers useful in the present invention encompass those containing the following saccharides: glucose, galactose, mannose, arabinose, xylose, fucose, fructose, glucosamine, galactosamine, glucuronic acid, galacturonic acid, and 5 or 6 membered ring polyalcohols. Also included are hydroxymethyl, hydroxyethyl and hydroxypropyl derivatives of the above sugars. When saccharides are bonded to each other in the copolymers, they may be bonded via any of several arrangements, such as 1,4-a; 1,4-β; 1,3-a; 1,3β and 1,6 linkages. The synthetic cationic monomers for use in these copolymers can include dimethyidiallylammonium chloride, dimethylaminoethylmethyacrylate, diethyldiallylammonium chloride, N,N-diallyl,N-N-dialklyl ammonium halides, and the like. A preferred cationic polymer is Polyquaternium 7 prepared with dimethyldialkylammonium chloride and acrylamide monomers.

Examples of members of the class of copolymers of saccharides and synthetic cationic monomers include those composed of cellulose derivatives (e.g. hydroxyethyl cellulose) and N,N-diallyl,N-N-dialkyl ammonium chloride available from National Starch Corporation under the tradename Celquat.

Further cationic synthetic polymers useful in the present invention are cationic polyalkylene imines, ethoxypolyalkelene imines, and poly{N-[3-(dimethylammonio)-propyl]-N'-[3-(ethyleneoxyethylene dimethylammoniumo)propyl]urea dichloride] the latter of which is available form Miranol Chemical Company, Inc. under the trademark of Miranol A-15, CAS Reg. No. 68555-336-2. Preferred cationic polymeric skin conditioning agents of the present invention are those cationic polysaccharides of the cationic guar gum class with molecular weights of 1,000 to 3,000,000. More preferred molecular weights are from 2,500 to 350,000. These polymers have a polysaccharide backbone comprised of galactomannan units and a degree of cationic substitution ranging from about 0.04 per anydroglucose unit to about 0.80 per anydroglucose unit with the substituent cationic group being the adduct of 2,3-epoxypropyl-trimethyl ammonium chloride to the natural polysaccharide backbone. Examples are JAGUAR C-14-S, C-15 and C-17 sold by Celanese Corporation, which trade literature reports have 1% viscosities of from 125 cps to about 3500±500 cps.

Still further examples of cationic polymers include the polymerized materials such as certain quaternary ammonium salts, copolymers of various materials such as hydroxyethyl cellulose and dialkyldimethyl ammonium chloride, acrylamide and beta methacryloxyethyl trimethyl ammonium methosulfate, the quaternary ammonium salt of methyl and stearyl dimethylaminoethyl methacrylate quaternized with dimethyl sulfate, quaternary ammonium polymer formed by the reaction of diethyl sulfate, a copolymer of vinylpyrrolidone and dimethyl aminoethylmethacrylate, quaternized guars and guar gums and the like. Exemplary of cationic polymers which can be used to make the complexes of this invention include, as disclosed in the CTFA International Cosmetic Ingredient Dictionary (Fourth Edition, 1991, pages 46–464); Polyquaternium -1, -2, -4 (a copolymer of hydroxyethylcellulose and diallyldimethyl ammonium chloride), -5 (the copolymer of acrylamide and beta-methacrylyloxyethyl trimethyl ammonium methosulfate), -6 (a polymer of dimethyl diallyl ammonium chloride), -7 (the polymeric quaternary ammonium salt of acrylamide and dimethyl diallyl ammonium chloride monomers, -8 (the polymeric quaternary ammonium salt of methyl and stearyl dimethylaminoethyl methacrylate quaternized with dimethyl sulfate), -9 (the polymeric quaternary ammonium salt of polydimethylaminoethyl methacrylate quaternized with methyl bromide), -10 (a polymeric quaternary ammonium salt of hydroxyethyl cellulose reacted with a trimethyl ammonium substituted epoxide), -11 (a quaternary ammonium polymer formed by the reaction of diethyl sulfate and a copolymer of vinyl pyrrolidone and dimethyl aminoethylmethacrylate), -12 (a polymeric quaternary ammonium salt prepared by the reaction of ethyl methacrylate/abietyl methacrylate/diethylaminoethyl methacrylate copolymer with dimethyl sulfate), -13 (a polymeric quaternary ammonium salt prepared by the reaction of ethyl methacrylate/oleyl methacrylate/diethylaminoethyl methacrylate copolymer with dimethyl sulfate), -14, -15 (the copolymer of acrylamide and betamethacrylyloxyethyl trimethyl ammonium chloride), -16 (a polymeric quaternary ammonium salt formed from methylvinylimidazolium chloride and vinylpyrrolidone), -17, -18, -19 (polymeric quaternary ammonium salt prepared by the reaction of polyvinyl alcohol with 2,3-epoxy-propylamine), -20 (the polymeric quaternary ammonium salt prepared by the reaction of polyvinyl octadecyl ether with 2,3-epoxypropylamine), -22, -24 a polymeric quaternary ammonium salt of hydroxyethyl cellulose reacted with a lauryl dimethyl ammonium substituted epoxide), -27 (the block copolymer formed by the reaction of Polyquaternium-2 (q.v.) with Polyquaternium-17 (q.v.)), -28, -29 (is Chitosan (q.v.) that has been reacted with propylene oxide and quaternized with epichlorohydrin), and -30.

The preferred surfactant is an anionic surfactant such as soap, alklyisethionate such as sodium cocoylisethionate, a sulfonate, a sulfate (optionally ethoxylated) and the like.

The anionic surfactant can be present in the composition in various preferred quantities beyond those general quantities previously discussed for all surfactants of from about 1 to about 96 wt. %, specifically about 5 to about 85 wt. %. With respect to liquid, preferably aqueous, compositions, the anionic surfactant is from about 2 to about 20 wt. % of the composition, specifically about 5 to about 15 wt. %. For a solid composition, the anionic surfactant can be from about 5 to about 90 wt. %, preferably from about 10 to about 50 wt. % for a "syndet" bar, about 55 to about 80 wt. % for a "combar", and about 70 to about 90 wt. %, more preferably about 75 to about 85 wt. % in a solid composition wherein there is only one anionic surfactant therein, such as soap.

The quantity of component b, the hydrophobic agent, varies considerably depending upon the function it carries out in the composition. Quantities of from about 0.01 to about 10 wt. % of the composition can be employed as long as there is a perceived skin affect. Generally, the lesser ranges are directed to materials which are effective in very low quantities such as the antibacterial agents. For example, both triclosan and trichlorocarbanilide are effective at quantities of from about 0.01 to about 1.5 wt. % of a composition, preferably a solid composition. Preferred quantities of these materials are from about 0.05 to about 1.4 wt. %, more preferably from about 0.1 to about 1.0 wt. %. At the higher end of the wt. % range are generally grouped materials which are used in quantities of about 1.0 to about 10 wt. % such as free fatty acid and esters, particularly in a solid composition. Preferred ranges are from about 2 to about 8 wt. %. Hydrophobic agents useful in the broad range are materials such as silicones, preferably dimethylsiloxane with a minimum viscosity of about 15,000, preferably about 40,000 centistokes. The silicones are preferably employed in solid compositions and not only can bring about a better "skin feel" but also bring about a measurable, real protection of the skin through the conservation of water in the skin. Quantities of silicones are from about 0.5 to about 10 wt. % of the composition, preferably about 0.75 to about 4 wt. % and more preferably about 1.0 to about 3.0 wt. % of the composition.

Component c of the composition is the hydrocarbon containing material which together with component d, the cationic polymer, brings about an increased perceived effect of the component b material on the skin. It is believed that the increased perceived effectiveness is due to the increased deposition component c onto the skin. Various components can be used as component c in this invention. For example, such materials include petrolatums, microcrystalline waxes, paraffin waxes, permethyls as previously described. Microcrystalline waxes are well known materials well described in numerous references. Petrolatums are preferred in the compositions of this invention, particularly solid compositions. These are mixtures of hydrocarbons with various softening points or ranges. The quantity of component c can vary from about 0.1 to about 10 wt. % of the composition. Generally, from about 0.25 to about 4 wt. % is preferred.

Component d is the cationic polymer. Most preferred cationic polymer families are the non cellulosic, non sugar containing cationic polymers, for example, those designated as Polyquat 6 and Polyquat 7 in the CTFA International Cosmetic Ingredient Dictionary, 4th edition 1991, respectively polymeric dimethyl diallylammonium chloride and the polymeric quaternary ammonium salt of acrylamide and dimethyl diallyl ammonium chloride. The quantity of the cationic polymer is an effective amount together with the component c material to bring about an improved perceived skin effect. In general, quantities of from about 0.01 to about 3.0 wt. % of the composition is cationic polymer, preferably from about 0.02 to about 0.9 wt. % and most preferably from about 0.05 to about 0.75 wt. %. In general, it is preferred that the quantities of components c and d together bring about a greater perceived effect than that effect achieved with component c alone and component d alone.

The physical nature of the composition is not critical and can be a solid, liquid or gel. If a solid, it is preferred that the component b is a silicone. The amount of moisture in the solid can be about 6 to about 22 wt. %. The compositions are in general made by standard skin cleansing composition techniques. However, in order to maximize the benefit received from the inventive composition, it is preferred to mix component b, c and d together initially before having any of these components in contact with any other materials present in the composition, particularly component a. It is most preferred to mix components b and c and then add the component d to the mixture of b and c. As a further illustration, when making a solid composition such as a bar, it is preferred to add the b, c and d premanufactured mixture to one or more of the other materials of the composition in an amalgamator, particularly when component b is a silicone or an antibacterial agent. With respect to temperature at the time of addition, it is preferred to add at the amalgamation step at about 20–30° C., essentially room temperature, but can be done at a higher temperature such as about 80–85° C. in a crutcher, particularly when a silicone is employed as component c.

Below is a standard method of preparation for the invention when a solid composition is desired.

| Solid Composition | |
|---|---|
| | Wt. % |
| Soap Chips (85/15, tallow/coco soap 10% moisture) | 94.82% |
| TCC | 0.7% |
| Petrolatum | 1.4% |
| Polyquat 7 (8% active) | 1.4% |
| Citric Acid (50% soln.) | 0.15% |

Solid Composition

|  | Wt. % |
|---|---|
| TIO2 | 0.5% |
| Preservatives and fragrance | 1.03% |

TCC is dispersed in petrolatum and Polyquat 7 is then added. This mixture is added to the soap chips in an amalgamator at 25–28° C., followed by titanium dioxide, preservatives and fragrance. The soap chips are milled three times, plodded and pressed into soap bars.

Below is a standard method of preparation when a liquid composition is desired.

Liquid Composition

Part 1

| | |
|---|---|
| SLES-2 (25.6%) | 9.0% |
| Preservative | 0.1% |
| Sodium Cumene Sulfonate (43%) | 7.0% |

Part 2

| | |
|---|---|
| Anti dandruff agent | 0.5% |
| Cocoamidopropyl Betaine (30%) | 9.0% |
| Polyquat 6 (40%) | 1.0% |
| Polyquat 7 (8%) | 1.0% |

Part 3

| | |
|---|---|
| Isosteareth-2 | 0.8% |
| C-20-40 alcohol | 4.0% |
| Distearyldimethyl Ammonium Chloride | 0.5% |
| Permethyl-106A | 2.0% |
| DP-300 | 1.0% |

Part 4

| | |
|---|---|
| Sodium Phosphate Dibasic | 0.2% |
| Dimethicone 60,000 cSt | 4.0% |
| Preservative | 1.0% |
| Fragrance | 0.5% |
| Water | Q.S. |

Procedure:

All the ingredients in part 1 are mixed at 20–25° C. The mixture is then heated to 85–90° C. and the components in part 2 are added stepwise to part 1 while maintaining the temperature. The ingredients of part 3 are mixed separately and the mixture is heated to 90–92° C. until the solution turns clear/hazy. This mixture is then added to a combination of part 1 and 2. This is followed by the addition of sodium phosphate dibasic and dimethicone at 75° C. and preservative and fragrance at 35° C. to part 1, 2 and 3.

Below are examples of the invention. Comparison examples of the invention and control experiments are also included. These examples are intended to illustrate the scope of the invention and are not intended to unduly limit the scope of the invention.

In the examples below, the following abbreviations are used:

TCC—Triclocarban, CAS No. 101-20-2, N-(4-chlorophenyl)-N'-(3,4-dichlorophenyl)urea DP300—Triclosan, CAS No. 3380-34-5, 5-chloro-2-(2,4-dichlorophenoxy)phenol Permethyl 4a—the polyisobutene of the prior formula in the specification wherein n is 16.

Polyquat 6—a polymer of dimethyl diallyl ammonium chloride. Present in compositions as a 40 wt. % active in water.

Polyquat 7—a copolymer of acrylamide and dimethyl diallylammonium chloride monomers. Present in compositions as an 8 wt. % active in water.

Petrolatum snow white, CAS Number 8009-03-8.

Soap—the sodium salt of fatty acids derived from tallow and/or vegetable oil in certain weight percents.

Silicone—a dimethylpolysiloxane having a viscosity of abut 60,000 centistokes.

Following is the methodology employed in the test system (s) used in the Examples below:

Deposition on Pig Skin

Materials and Methods

Skin Sample:

Full-thickness skin from 3–6 month old male Yucatan swine was obtained. The animals were raised under controlled environmental conditions and fed a special diet to maintain a relatively constant stratum corneum lipid composition. The skin was carefully removed from the euthanized animal by a veterinarian and immediately frozen in liquid nitrogen.

The frozen skin was allowed to thaw to room temperature prior to careful removal of the subcutaneous fat using a sharp scalpel. The tissue was rinsed with "millipore" water, water of ultra purity, and cut into squares of approximately 1.5 sq. in. The skin then wrapped in plastic wrap and frozen until required.

Preparation of Soap Samples:

A soap chip was pre-milled through a laboratory scale 3-roll mill. The additives were added to the soap chip and mixed well. The soap chip was then milled three times through a 3-roll mill to ensure a uniform product. Soap solutions (5%) were prepared using the milled soap chip and water having 100 ppm of hardness [Ca,Mg].

Sample Stage:

A specially designed metallic sample stage as substantially shown and described in Hilliard (Clairol) U.S. Pat. No. 4,836,014 was used for treatment of the skin samples. The sample stage allows simultaneous treatment of twelve samples with a uniform area of skin exposed to treatment (about 5.72 cm$^2$). The bottom plate consists of twelve wells with twelve corresponding wells on the top plate. The sample stage is held together via wing-nut screws.

Experimental Procedure:

The skins were removed from the freezer and allowed to defrost at room temperature for approximately 0.5 hour. Once defrosted, the skins were rinsed with several milliliters of ultrapure water. The skins were then mounted on the sample stage with the stratum corneum facing up and clamped tightly into place.

The following procedure was employed for deposition of silicone, TCC and DP-300:

Two milliliters of the 5% (by weight) soap solutions were pipetted onto each skin specimen. The entire sample stage was covered with aluminum foil to prevent evaporation during treatment. The sample stage was placed in a temperature-controlled shaker (Lab-Line Instruments) equilibrated at the desired temperature (500° C. for 93 wt. % soap, 7 wt. % free fatty acid, 60 wt. % of the soap derived from tallow and 40 wt. % of the soap derived from coconut oil abbreviated as 60/40/17 and 600° C. for 85/15 soap bases wherein 85 wt. % is derived from tallow and 15 wt. % is derived from coconut oil with no additional free fatty acid). The speed of rotation was set to 50 rpm and the specimens were treated for 1 hour. Following treatment, the soap solutions were pipetted off the skin specimens and each specimen was then rinsed three times with 1.5 ml aliquots of ultrapure water.

Silicone deposition on the skin specimens was determined by the following procedure: 1.5 ml aliquots of kerosene were added to each specimen and were subsequently treated for 5 minutes in the temperature-controlled shaker equilibrated at 250° C. and set to a shaker speed of 75 rpm for five minutes. Following treatment, the solutions were pipetted off each specimen and into vials. These silicone extractions were repeated two additional times and extraction solutions combined for a given specimen. Silicone concentrations were determined by ICP (inductively Coupled Argon Plasma) analysis.

The procedure for extracting TCC and DP-300 from the skin specimens was the same as that for silicone with the following modifications: 1 hexane: 1 chloroform: 2 isopropanol (by volume) was used in place of kerosene to extract the antibacterial actives from the specimens. Treatment times were decreased from 5 minutes to 3 minutes to minimize evaporation of the solvent system. A total of 4 extractions instead of 3 for the silicone were performed for each specimen. TCC and DP-300 concentrations of the extracts were determined by UV absorption spectroscopy using $e265$ nm=0.14289 ppm$^{-1}$ cm$^{-1}$ for TCC and $e280$ nm=0.01553 ppm$^{-1}$ cm$^{-1}$ for DP-300.

Additionally, studies were performed to assure that silicone, TCC and DP-300 could be recovered from the skin specimens at concentrations comparable to those deposited. The procedure for these recovery studies was as follows: 0.5 ml of 0.25% soap solutions were pipetted onto each specimen. The specimens were not covered with aluminum foil during the 1 hour treatment period. Extraction of the silicone, TCC. or DP-300 was performed as described above immediately following treatment, without rinsing the specimens with water.

Procedure for Deposition of TCC. or DP-300 onto Wool Substrates

Soap solutions (5–5.9%) were prepared on low heat so as to avoid TCC decomposition. Generally, soap solution temperatures of 50° C. and heating times greater than 30 minutes were not exceeded. Wool swatches (48 cm$^2$) were immersed in soap solutions. Solutions were placed in an oven, equilibrated to 40–45° C., for 2 hours or alternatively temperatures of 20–25° C. for 15 minutes. Following treatment, liquid was decanted from solution jar and swatches were rinsed with a 100 ml aliquot of ultrapure water. Two additional rinses were performed with a 5 minute stirring. Tweezers were used to remove swatches from jar and left to dry overnight.

TCC or DP-300 was extracted from the dried swatches by adding 50g of 2 isopropanol: 1 hexane: 1 chloroform (by volume) to each swatch and stirring for 15 minutes. Swatches were removed and concentrations of TCC or DP-300 were determined using UV absorption spectroscopy as described previously.

| Product Compositions for Examples 1, 4, and 5 | |
| --- | --- |
| Ingredient | Weight % |
| Soap Chip (85/15 Tallow/Coco) 10% moisture | 96.5 |
| TCC | 0.7 |
| Delivery System | 2.8 |

| Soap Chip Compositions for Example 6 | |
| --- | --- |
| Ingredient | Wt. % |
| Soap Chips - 1 | |
| Soap (60/40, tallow/Coco) | 83 |
| Free Fatty Acids | 7 |
| Water | 10 |
| | 100 |
| Soap Chips - 2 | |
| Soap (85/15, tallow/coco) | 90 |
| H$_2$O | 10 |
| | 100 |

EXAMPLE 1

| Deposition of TCC onto a wool swatch after a two hour contact time (40–45° C.) with 5.9 wt. % product solution | |
| --- | --- |
| Delivery System | mg TCC/sq. cm. Wool Swatch |
| Polyquat 6 (2.8 wt. %) | 1.77 |
| Polyquat 7 (2.8 wt. %) | 5.7 |
| Permethyl No. 104A (2.8 wt. %) | 6.4 |
| Permethyl No. 104A (1.4 wt. %)/polyquat 6 (1.4 wt. %) | 4.7 |
| Permethyl No. 104A (1.4 wt. %)/polyquat 7 (1.4 wt. %) | 9.1 |

EXAMPLE 2

| Deposition of DP-300 onto a wool swatch at 20–25° C. after a fifteen minute contact time from a mixture of 5 wt. % soap solution, 0.7 wt. % DP-300 and 2.8 wt. % delivery system | |
| --- | --- |
| Delivery System | mg DP-300 Deposited/sq. cm. wool Swatch |
| Permethyl No. 104A (2.8 wt %) (Polyisobutene) | 89.87 |
| Polyquat 6 (2.8 wt. %) | 44 |
| Polyquat 7 (2.8 wt. %) | 251 |
| Permethyl No. 104A (1.4 wt. %)/Polyquat 6 (1.4 wt. %) | 557 |

EXAMPLE 3

| Deposition of TCC onto a wool swatch at 20–25° C. after a fifteen minute contact time from a mixture of 5 wt. % soap solution, 0.7 wt. % TCC and 2.8 wt. % delivery system | |
| --- | --- |
| Delivery System | mg TCC/sq. cm. Wool Swatch |
| Permethyl No. 104A (2.8 wt. %) | 116 |
| Polyquat 6 (2.8 wt. %) | 111 |

-continued

Deposition of TCC onto a wool swatch at 20–25° C.
after a fifteen minute contact time from a mixture of
5 wt. % soap solution, 0.7 wt. % TCC and 2.8 wt. % delivery system

| Delivery System | mg TCC/sq. cm. Wool Swatch |
|---|---|
| Permethyl No. 104A (1.4 wt. %) and Polyquat 6 (1.4 wt. %) | 416 |

EXAMPLE 4

TCC Deposition Results
Pig Skin Studies
Deposition of TCC (60° C.) from
5.0 wt. % Product Solution

| Delivery System | Deposition of TCC (mg TCC/cm$^2$ pig skin) |
|---|---|
| Petrolatum (2.8 wt. %) | 12.7 ± 2.3 |
| Polyquat 7 (2.8 wt. %) | 29.2 ± 3.1 |
| Petrolatum (1.4 wt. %)/Polyquat 7 (1.4 wt. %) | 40.0 ± 2.6 |

EXAMPLE 5

TCC Deposition Results
Wool Binding Method
Deposition of TCC (45° C.) from
5.0 wt. % Product Solution

| Delivery System | Deposition of TCC (mg TCC/cm$^2$ wool swatch) |
|---|---|
| Permethyl No. 104A (2.8 wt. %) | 1.7 ± 0.2 |
| Polyquat 6 (2.8 wt. %) | 1.8 ± 0.4 |
| Polyquat 7 (2.8 wt. %) | 4.2 ± 1.3 |
| Permethyl No. 104A (1.4 wt. %)/Polyquat 6 (1.4 wt. %) | 4.6 ± 1.2 |
| Permethyl No. 104A (1.4 wt. %)/Polyquat 7 (1.4 wt. %) | 9.1 ± 0.5 |
| Petrolatum (1.4 wt. %)/Polyquat 7 (1.4 wt. %) | 13.1 ± 3.9 |

Example 6

Silicone Deposition
Results on Pig Skin

| Sample | # Samples | ug dimethicone per skin sample | ug dimethicone per 1 cm$^2$ of skin |
|---|---|---|---|
| Soap Chips 1 (95 wt. %) plus 5 wt. % dimethicone | 3 | 17.1 +/− 2.1[a] | 3.0 |
| Soap Chips 1 (92 wt. %) plus 5 wt. % dimethicone plus 1.5 wt. % Polyquat 7 and 1.5 wt. % Permethyl 104A | 3 | 52.0 +/− 18.3[b] | 9.1 |
| Soap Chips 2 (95 wt. %) plus 5 wt. % dimethicone | 4 | 35.4 +/− 15.1[a] | 6.2 |
| Soap Chips 2 (92 wt. %) plus 5 wt. % dimethicone plus 1.5 wt. % Polyquat 7 and 1.5 wt. % Permethyl 104A | 4 | 94.0 +/− 29.4[b] | 16.4 |
| Soap Chips 2 (93 wt. %) plus 2.5 wt. % dimethicone plus 1.5 wt. % Polyquat 7 and 1.5 wt. % Permethyl 104A | 4 | 43.8 +/− 11.9[a] | 7.7 |
| Soap Chips 2 (94.5 wt. %) plus 2.5 wt. % dimethicone plus 1.5 wt. % Polyquat 7 and 1.5 wt. % Permethyl 104A | 3 | 62.5 +/− 12.4[a] | 10.9 |
| Soap Chips 2 (93 wt. %) plus 2.5 wt. % dimethicone plus 3.0 wt. % Polyquat 7 and 1.5 wt. % Permethyl 104A | 3 | 109.5 +/− 16.5[b] | 19.2 |

[a],[b]indicate a significant difference
Dimethicone is dimethylsiloxane of viscosity 60,000 centistokes.

Further testing is conducted with a composition comprising soap consisting of 85 wt. % derived from a tallow base carboxylic acid and 15 wt. % from a coconut oil based carboxylic acid and 10 wt. % water with a limited amount of preservatives, fragrances and the like also present.

The test compositions are prepared by adding a superfatting agent such as citric acid or phosphoric acid, a hydrophobic agent, such as dimethicone, a hydrocarbonaceous material such as petrolatum, and a cationic polymer such as Polyquat 6, to the desired wt. % levels based upon the final bar weight. When utilizing dimethicone (dimethylpolysiloxane) at a viscosity of 60,000 centistokes, petrolatum, citric acid or phosphoric acid and Polyquat 6, the preferred quantities of each are respectively 1 wt. %, 3.5 wt. %, 1 wt. % generated superfat and 0.6 wt. % Polyquat 6 (40% active).

Bars are prepared with the final preferred composition together with a series of fragrances. Control bars are prepared with the same series of fragrances but without the dimethicone, petrolatum and Polyquat package but with or without 1 wt. % generated superfat. Upon in vivo testing, the bars of the invention surprisingly show increased intensity of the fragrance upon aging in comparison to the control. Additionally, enhanced character and bloom is present for the bar of the invention in comparison to the control bar. By character is generally meant less odor from animal based soaps thereby providing less distortion of the fragrance and maintenance of the consistency of the fragrance aroma. Enhanced bloom indicates that both the "top note" and the "bottom notes" of the fragrances are continually sensed.

Further testing of the sensory package alone (dimethicone, petrolatum and Polyquat 6) both in vitro and in vivo, as well as bars containing the package as opposed to a control bar without the package and without 1% superfat, establishes advantages. For example, a neat mixture of dimethicone (60,000 centistokes), petrolatum and Polyquat 6 in weight ratio, respectively, of 1:2:0.6 inhibits climatic induced dryness as well as inhibits the loss of Natural Moisturizing Factor (NMF) in in vitro testing.

The procedure which one follows for measuring climatic induced dryness is the following:

Untreated pig skins are used as controls. Pig skins are kept at 10° C./17% relative humidity for one hour. Baseline conductance measurements are taken by SKICON meter. Neat actives are applied (2 mg/sq. cm) of pig skin at room temperature. The samples are equilibrated for one hour at room temperature. After 24 hours at 100° C./17%, conductance values are measured by a SKICON conductance meter.

Substantial increases in conductance are observed indicating that climatic induced dryness is substantially inhibited.

The procedure which one follows for the measurement of the inhibition of NMF (amino acids, urea, sodium pyrrolidone carboxylic acid, inorganic ions) extraction is the following:

The neat active mixture is applied to pig skin at 2 mg/sq. cm. After one hour skins are treated with 2 ml of 1% 85/15 soap solution at 45° C., with shaking for 15 minutes. Nontreated pig skin (no neat mixture) is treated with soap in the same manner. The soap solutions are removed and analyzed for amino acids and urea by a fluorescent assay similar to that described in M. Kawal and G. Imokawa, J. Soc. Cosmetic Chem., 35, 147–156 (1984). The assay shows the treated pig skin has far less loss of NMF than the pig skin which did not have the package of dimethicone, petrolatum and Polyquat.

A further in vitro test using the bar of the invention to show the deposition of hydrophobic material through the inhibition of dye uptake in comparison to the control bar is demonstrated by the following test procedure:

Pig skins are washed four times with invention bar (30 second rub, 30 second lather, 15 second rinse). A 1 cm diameter filter paper disc is placed in a 1% solution of D&C. Red #28 dye. The disc is immediately applied to the pig skin and rinsed for 15 seconds. The remaining dye on skin is removed with kimwipe. The color of skin is recorded with a Minolta Chromameter. The steps are repeated on fresh pig skin using the control bar. The dye uptake on the skin treated with the bar of the invention is far less than the control bar treated skin.

The effect of the bar of the invention (1% superfat, 1% dimethicone 60,000 centistokes, 3.5% petrolatum, 0.6% Polyquat 6) on barrier integrity of the skin is measured by the following procedure:

Pig skin is treated with 5% product aqueous solutions. The skin is exposed for 24 hour to the solutions. Following this exposure, the skin is exposed to tritiated water and skin penetration by the tritiated water is measured. The barrier integrity is assessed in terms of the permeability coefficient (Kp) of $H_2O$. The procedure is repeated using 5% control solutions on fresh pig skin. The results show that the bar of the invention mitigates induced barrier damage in comparison to the control bar.

The effect of the bar of the invention, previously identified, is assessed for its effect on soap penetration of the skin using the following procedure:

5% soap invention bar solutions are spiked with $^{14}C$-Lauric Acid and tritiated water. The penetration of the pig skin is followed by tracking the lauric acid (laurate) and water. Punch biopsies of the pig skin are analyzed to determine soap retained in the skin. The experiment is repeated with fresh pig skin and control bar solution. The results show that the invention bar significantly inhibits the penetration of lauric acid through the skin, provides less retention of the lauric acid while providing no significant difference in retention of water in the skin, all in comparison to the control. Additionally, as measured by the Kp of water, less skin damage is induced.

In vivo tests are also employed to measure the effect of the neat package on various skin factors. For example, conductance measured by SKICON is used to measure the degree of skin hydration. A water desorption test is used to measure the water holding capacity of skin. Fluorescence is used to measure the extraction of NMF from skin. Water repellency of the skin is also measured. Finally, dye uptake is also measured. In each of these test systems, the neat package of dimethicone petrolatum and Polyquat 6 (1:3.5:0.6) shows a positive effect for the skin, for example, hydration, attracting and holding water, locking moisture into the skin and providing a protective shield for the skin.

In vivo tests employing the bar with the active package are also tested versus the control bar in the dye uptake test. There is clearly less dye uptake when skin is washed with the bar of the invention as opposed to the control bar.

Additionally, in vivo tests are run on the invention bar compared to the control bar as to the characteristic of mildness. There is significantly less irritation after repeated use of the invention bar as measured by erythema as visually assessed by a clinician and, as assessed by redness instrumentally at the termination of the test. Barrier damage as measured by transepidermal water loss at the termination of the test is reduced. Still further, panelists significantly prefer the invention bar over the control bar on the basis of mildness.

In summary, the invention solid composition utilizing a hydrophobic component (dimethicone), a hydrocarbonaceous component (petrolatum) and a cationic polymer (Polyquat 6) is clearly superior as a protective skin shield, less irritating, and induces less damage wherein the surfactant is soap (about 70 to about 90 wt. %) than a soap bar without these agents. The invention bar had 1 wt. % superfatting agent therein. The control bar did not.

What is claimed is:

1. A solid cleansing composition which comprises
   a. about 70 to about 90 wt. % soap,
   b. about 0.01 to about 1.5 wt. % of triclocarban or triclosan,
   c. about 0.5 to about 5 wt. % of petrolatum, and
   d. about 0.01 to about 3.0 wt. % of cationic polymer.
2. The composition in accordance with claim 1 wherein (b) is triclocarban.
3. The composition in accordance with claim 1 wherein petrolatum is about 0.75 to 4 about 4 wt. % of the composition.
4. The composition in accordance with claim 1 wherein the cationic polymer is about 0.02 to about 0.9 wt. %.
5. The composition in accordance with claim 1 wherein the cationic polymer is polymeric dimethyl diallyl ammonium chloride (polyquat 6) or the polymeric quaternary ammonium salt of acrylamide and dimethyl diallyl ammonium chloride (polyquat 7).
6. The composition in accordance with claim 5 wherein the cationic polymer is polymeric dimethyl diallyl ammonium chloride.
7. The composition in accordance with claim 6 wherein the solid is in bar form.
8. The composition in accordance with claim 2 wherein petrolatum is about 0.75 to about 4 wt. % of the composition.
9. The composition in accordance with claim 2 wherein the cationic polymer is about 0.02 to about 0.9 wt. %.
10. The composition in accordance with claim 2 wherein the cationic polymer is polymeric dimethyl diallyl ammonium chloride (polyquat 6) or the polymeric quaternary ammonium salt of acrylamide and dimethyl diallyl ammonium chloride (polyquat 7).
11. The composition in accordance with claim 10 wherein the cationic polymer is polymeric dimethyl diallyl ammonium chloride.
12. The composition in accordance with claim 11 wherein the solid is in bar form.

* * * * *